United States Patent [19]

Seto et al.

[11] Patent Number: 4,673,634

[45] Date of Patent: Jun. 16, 1987

[54] PURIFIED ANTIGEN FROM NON-A, NON-B HEPATITIS CAUSING FACTOR

[75] Inventors: Belinda Seto, Bethesda; Robert J. Gerety, Potomac, both of Md.

[73] Assignee: The United States of America as represented by the Department of Health and Human Services, Washington, D.C.

[21] Appl. No.: 709,678

[22] Filed: Mar. 8, 1985

[51] Int. Cl.$^4$ .................. A61K 39/29; C12Q 1/70; G01N 33/531; G01N 33/576

[52] U.S. Cl. .................................. 435/5; 424/86; 424/89; 435/7; 435/810; 436/543; 436/547; 436/820; 530/395; 530/826

[58] Field of Search ................. 436/543, 547, 820; 530/387, 806, 826, 395; 435/5, 7, 810; 424/89

[56] References Cited

U.S. PATENT DOCUMENTS 4,464,474  8/1974  Coursaget et al. ............ 436/820

FOREIGN PATENT DOCUMENTS 0066296  12/1982  European Pat. Off. ............ 435/7
8202774   8/1982  Int'l Pat. Institute ............ 435/7
8203330  10/1982  Int'l Pat. Institute ............ 435/7
8404326  11/1984  Int'l Pat. Institute ............ 435/7

OTHER PUBLICATIONS

Feinstone, et al., Non-A, Maybe-B Hepatitis, N. Engl. J. Med., 1984, 311:185–188.
Shirachi, et al., Hepatitis "C" Antigen in Non-A, Non-B Post-Transfusion Hepatitis, Lancet, (10/21/78), 854–6.
Deinhardt, et al., Viral Hepatitis, Bulletin of the World Health Organization, 60(5):661–691, (1982).
Tabor, E., Developments in Non-A, Non-B Hepatitis Screening, Lab World, 31:25–27, 1980.
Suh, et al., Specificity of an Immunoprecipitin Test for Non-A Non-B Hepatitis, Lancet, (1/24/81), 178–80.
Prince, et al., Long-Incubation Post-Transfusion Hepatitis Without Serological Evidence of Exposure to Hepatitis-B Virus, Lancet, (8/03/74), 241–6.
Alter et al., Clinical and Serological Analysis of Transfusion-Associated Hepatitis, Lancet, (11/01/75), 838–41.

Primary Examiner—Sidney Marantz
Assistant Examiner—David A. Saunders
Attorney, Agent, or Firm—Holman & Stern

[57] ABSTRACT

The present invention discloses an isolated and purified antigen specific to non-A, non-B hepatitis (NANBH) causing agent. The utility of the antigen as a diagnostic serologic marker and as a screening device for detecting the carrier or source of non-A, non-B hepatitis or infective factor thereof, particularly in a blood bank or plasmapheresis setting and preventing transmission of NANBH by isolating the source is described. Use of the antigen as vaccine to induce protective antibodies capable of neutralizing NANBH infectivity is also disclosed. A kit for detecting the presence or identifying the carriers or sources of non-A, non-B hepatitis or causative agent thereof is also disclosed.

5 Claims, 5 Drawing Figures

200K —
92.5K —
68K —
43K —
25.7K —
18.4K —
12.3K —

PURIFIED ANTIGEN FROM NON-A, NON-B HEPATITIS CAUSING FACTOR

BACKGROUND OF THE INVENTION

1. Technical Field

The present invention is directed to isolation, purification and characterization of a specific serologic marker for non-A, non-B hepatitis (NANBH). More particularly, the present invention is related to obtaining an isolated, purified antigen associated with non-A, non-B hepatitis causing factor for use in in vitro detection kits and for use as a vaccine against NANBH.

2. Prior Art

Hepatitis non-A, non-B accounts for 20%–40% of sporadic cases of hepatitis among adults in the United States. This type of hepatitis accounts for 90% of post-transfusion hepatitis. An alarming 50% of these cases develop chronic NANBH, and such individuals remain as potential sources of infection. Evidence for the existence of a transmissible agent in this disease has been demonstrated by the infection of chimpanzees by inoculation with serum from a chronic non-A, non-B hepatitis patient, and by serial passage to additional chimpanzees. It may be further noted that chimpanzees have been accepted as surrogate human models for testing purposes and that the diagnosis of NANBH is based upon the exclusion of other human hepatotropic viruses usually by avaialble serologic tests specific for these other agents.

Shirachi et al, Lancet, 853–856 (1978); and Tabor et al, J. Med. Virol. 4, 161–169 (1979) amongst others reported the presence of antigen-antibody tests, all of which suffer the disadvantages of non-specificity, insensitivity, and most importantly, the uncertainty of viral or host origin of the antigens and antibodies. The present invention discloses purified antigen which for the first time provides direct means for detecting Non-A, Non-B hepatitis without cross-reacting with other viral or host antigens.

It may be noted that heretofore the diagnosis of this disease relied on the serologic exclusion of other hepatotropic human viruses such as hepatitis A, hepatitis B, cytomegalovirus and Epstein-Barr virus.

SUMMARY OF THE INVENTION

It is, therefore, an object of the present invention to provide a specific serologic marker for directly detecting or diagnosing non-A, non-B hepatitis (NANBH).

It is another object of the present invention to prepare an isolated, purified antigen specifically associated with NANBH disease.

It is a still further object to induce host immune responses (e.g., antibodies) against NANBH utilizing the purified antigen of the present invention for use in in vitro detection kits and for immunization against NANBH.

It is yet another object of the present invention to prevent transmission of NANBH by detecting the presence of NANBH factor in sources or carriers thereof by utilizing the purified antigen of the present invention or a product derived therefrom.

It is a still further object of the present invention to provide protection against NANBH utilizing the purified antigen as an immunogen to induce specific protective antibodies.

A further object of the present invention is to enable blood banks or plasmapheresis establishments to screen blood, blood products or donors thereof for the presence of NANBH factor utilizing the isolated and purified antigen or a product derived therefrom.

Other objects and advantages will become evident as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1A:
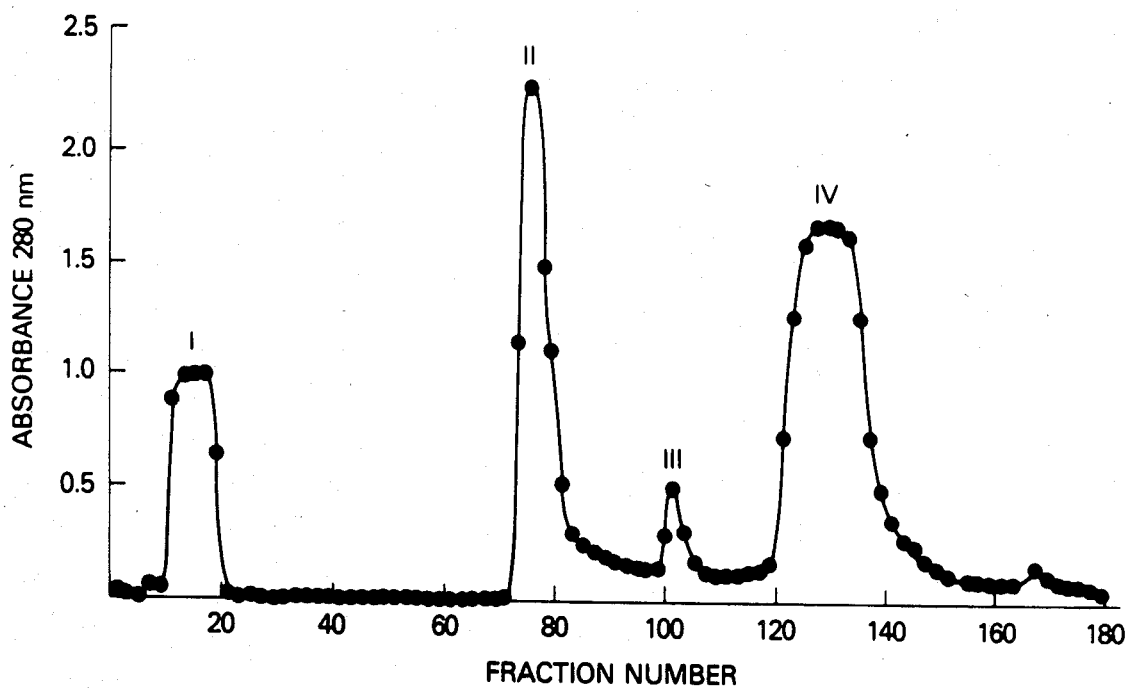
FIG. 1A shows DEAE-cellulose chromatography of the serum of a NANBH patient (inoculum I) and FIG. 1B shows column profile of the serum of a hepatitis B patient.

These and other objects of the present invention are achieved by an isolated, purified non-A, non-B hepatitis associated antigen present on the surface of virus particles at a density of 1.14 g/ml and in soluble form having the following properties:

(a) molecular weight of the glycoprotein monomer on sodium dodecyl sulphate polyacrylamide gel being about 77,000;

(b) the monomer is reactive with the rhesus monkey immune serum;

(c) being a glycoprotein containing about 2% carbohydrate comprising predominantly mannose and about equal ratio of fucose and galactose;

(d) having an aromatic amino acid composition comprising molecular ratios of phenylalanine, tyrosine and tryptophan of about 3:3:1 respectively; and (e) being an immunogen.

Although several alternate or equivalent methods and materials could be used for the practice of the present invention, the following are preferred embodiments thereof. All publications cited hereunder are incorporated herein by reference.

ISOLATION OF NANBH-ASSOCIATED ANTIGEN

Chromatography on diethyl aminoethyl (DEAE)-cellulose

Human serum (inoculum I) from a patient with chronic NANBH whose blood or serum had previously transmitted NANBH to a human by accidental inoculation and to a series of experimentally inoculated chimpanzees was used. Ten ml of this serum was diluted to a total volume of 40 ml with 5 mM Tris-phosphate buffer, pH 8.5. The serum was absorbed to a DEAE-cellulose column ($DE_{52}$, 1.5 cm$\times$22 cm) previously equilibrated with the Tris-phosphate buffer. Fractionation was then accomplished by a step-wise gradient of Tris-phosphate buffers as described by Sober, et al (Fed. Proc. 17, 1115–1126, 1958): (a) 81 ml 5 mM Tris-phosphate pH 8,5, (b) 72 ml 20 mM Tris-phosphate, pH 8.0, (c) 63 ml 30 mM Tris-phosphate, pH 7.6, (d) 270 ml 50 mM Tris-phosphate, pH 7.1 and (e) 315 ml 80 mM-Tris-phosphate, pH 6.6. Fractions of 4.5 ml each were collected and the absorbance at 280 nm determined in a Hitachi 100-80A spectrophotometer.

Other sera were similarly fractionated. These included four additional proven infectious NANBH sera, three sera from patients with hepatitis B and one serum from an asymptomatic human without hepatitis. A summary of the chromatographic profiles is presented in Table I.

Con A-Sepharose Affinity Chromatography

After elution from the DEAE column, fractions containing protein peak III (see Table I and FIG. 1A), a peak unique to NANBH sera, were pooled and concentrated using a PM10 Amicon filter.

TABLE I

A SUMMARY OF THE CHROMATOGRAPHIC PROFILE IN HUMAN SERA ON DEAE-CELLULOSE

| Patient Diagnosis | Number of Sera Studied | Protein Peaks (No. Positive) I | II | III | IV | Percent Positive For Peak III |
|---|---|---|---|---|---|---|
| NANBH | 5+ | 5 | 5 | 4+ | 5 | 80% |
| Hepatitis B | 3 | 3 | 3 | 0 | 3 | 0% |
| Normal Control | 1 | 1 | 1 | 0 | 1 | 0% |

+Four sera documented to transmit NANBH to other humans and/or chimpanzee all contained protein peak III.

The concentrate was equilibrated to 50 mM potassium phosphate buffer, pH 7.1, and then absorbed to a 5 ml Con A-Sepharose (concanavalin A-linked agarose gel, Pharamacia, N.J.) column previously equilibrated with the same buffer containing 1 mM $CaCl_2$ and eluted by a two-step elution with potassium phosphate buffer containing first 10 mM α-methyl mannoside and then 20 mM α-methyl mannoside.

Rechromatography on DEAE-Cellulose

The second protein peak eluted from the Con A-Sepharose column was further purified by a second DEAE column using a linear gradient of 100 ml each of 20 mM to 50 mM potassium phosphate buffer, pH 7.1.

Detection of the NANBH-Associated Antigen During Purification

All protein fractions derived during the chromatographic procedures were tested for the presence of NANBH-associated antigen(s) by a counterelectrophoresis test as described by Tabor, U.S. Pat. No. 4,395,395 which is incorporated herein by reference, using an antiserum from a chimpanzee (chimpanzee 916) previously exposed to the human NANBH agent in inoculum I.

Molecular Weight Determinations

Molecular weight of the monomer was determined by sodium dodecyl sulfate-polyacrylamide gel electrophoresis (SDS-PAGE) performed on the purified glycoprotein according to the method of Laemmli (as described by Laemmli in Nature 227, 680–685). Slab gels of 9% polyacrylamide-containing a 0.1% sodium dodecyl sulfate were performed at 25 mA for 2.5 hours. Gels were then stained with 0.1% Coomassie brilliant blue in 10% acetic acid. Protein markers of known molecular weights, namely, myosin (200K), phosphorylase b (92.5K) bovine serum albumin (68K), ovalbumin (43K), α-chymotripsinogen (25.7K), lactoglobulin (18.4K), and cytochrome C (12K) were used as standards.

Western Blot

The monomer of the glycoprotein was electrophoresed in 12% SDS-PAGE and blotted to nitrocellulose essentially according to the procedure of Towbin et al (Proc. Natl. Acad. Sci. USA. 76:4350–4354, 1979).

Induction of Antibodies to the Antigen Glycoprotein

Any suitable host can be used for inducing antibodies following standard protocols well known in the art. For the purposes of testing, rhesus monkeys were employed. For three consecutive weeks, prebleeds were obtained from two rhesus monkeys (Nos. 877, 245). Each was then inoculated intramuscularly at 0 time, 3 weeks and 10 weeks with a total of 180 ug of purified antigen (glycoprotein) emulsified first in complete Freund's aduvant and subsequently in incomplete Freund's adjuvant. Sera from the rhesus monkeys were tested weekly by "solid-phase" radioimmunoassay (RIA) for antibodies against the immunizing antigen. For this purpose, the glycoprotein was radioiodinated using lactoperoxidase and glucose oxidase-immobilized beads (ENZYMOBEADS, Bio-Rad Laboratories, Richmond, Calif., according to procedures recommended by the manufacturer. Rhesus monkey 877 antiserum was selected for use although both rhesus monkeys made antibodies to the glycoprotein. Either rhesus monkey 877 serum or the 7S IgG fraction prepared from the antiserum was tested and the antibody titer expressed as the percentage of radiolabelled antigen bound. The maximum radioactivity bound was 85% at a week 7.

Immunoreactivity of Rhesus Monkey Antibodies to the Glycoprotein

7S IgG from rhesus monkey 877 was radioiodinated using ENZYMOBEADS and reacted in a "solid-phase" radioimmunoassay with sera from patients with NANBH, with hepatitis B, with negative control sera and with sucrose gradient fractions of inoculum I.

By definition, antibodies are, of course, specific to a particular antigen. Hence, the antibodies in the rhesus monkey immune serum will recognize and react only with an antigen identical or similar with the isolated, and purified NANBH glycoprotein. Therefore, antigens different from the NANBH glycoprotein described herein will not react with the rhesus monkey immune serum and can be identified and differentiated.

In neither case will the rhesus monkey pre-immune serum react with the antigens.

Solid-phase Radioimmunoassay

A modified procedure of Coursaget et al (J. Med. Virol 6, 53–60, 1980) is followed. To detect the NANBH-associated antigen, polystyrene beads (3.2 mm diameter) coated with unlabelled anti-glycoprotein rhesus monkey antiserum (1:20 dilution) were incubated overnight at 4° C. with 50 ul of serum to be tested. The beads were washed three times with phosphate buffered saline, pH 7.4, and incubated sequentially for 3 h at 37° C. and overnight at 4° C. with 50 ul of radiolabelled anti-glycoprotein IgG (1:20 dilution). The beads were rewashed, and adherent radioactivity determined in a gamma counter. Samples with greater than twice the CPM of the negative control serum were considered positive (see Table II).

Spectroscopic Analysis

The NANBH glycoprotein was further characterized by quantitative spectroscopic determination of aromatic amino acid residues in the glycoprotein according to Levine, et al, Biochem 21: 2600–2606 (1982). For this purpose 70 ug of the protein was dialyzed against 1 liter of guanidine-HCl made in 20 mM potassium phosphate buffer, pH 6.5 at room temperature overnight.

TABLE II
DETECTION OF NANBH GLYCOPROTEIN IN PATIENT SERA USING RIA

| Patient Diagnosis | Number of Sera Studied | Number Sera Positive |
|---|---|---|
| NANBH | | |
| Chronic | 15 | 15 |
| Acute | 28 | 3 |
| Hepatitis B | 11 | 0 |
| Hepatitis A | 4 | 0 |
| Controls | 86 | 2 |

Absorption spectra were obtained with a Hewlett-Packard 8450A spectrophotometer and the relative concentrations of phenylalanine, tyrosine and tryptophan were found to be about 3:3:1, respectively.

| | multicomponent analysis | | |
|---|---|---|---|
| | phe ($\mu$M) | Tyr ($\mu$M) | Trp ($\mu$M) |
| NANBH glycoprotein | 15.2 | 15.6 | 5.1 |

Amino Acid Analysis

The NANBH glycoprotein (70 ug) was hydrolyzed in vaccuo with 100 $\mu$l constant boiling 6N HCl for 45 minutes at 155° C. The hydrolysate was dried and resuspended in trifluoroacetic acid for analysis. The amino acid composition was determined by post-column derivatization with o-phthalaldehyde, and the fluorescent derivatives were resolved on a C-18 reverse phase column with the IBM 9533 high-performance liquid chromatographic system as described by Jones, B, (1983) J. Chromat. 266:471. Table III shows relative amino acid composition of the NANBH antigen.

TABLE III
RELATIVE AMINO ACID COMPOSITION OF NANBH ANTIGEN (GLYCOPROTEIN)

| Amino Acid | Peak Area (Estimated Percent) |
|---|---|
| Asp | 12.9 |
| Glu | 9.5 |
| Ser | 7.3 |
| His | 1.5 |
| Gly | 9.8 |
| Thr | 4.9 |
| Arg | 5.6 |
| Ala | 9.5 |
| Tyr | 6.2 |
| Met | 0.9 |
| Val | 5.7 |
| Phe | 7.8 |
| Ile | 1.9 |
| Leu | 9.5 |
| Lys | 4.6 |
| Pro* | N.D. |
| Cys* | N.D. |
| Trp* | N.D. |
| TOTAL | 98 |

*N.D. = Not determined by this hydrolysis. O—phthalaldehyde will not react with a secondary amine such as proline, and 6N HCl hydrolysis destroys tryptophan and cysteine.

Neutral Sugar Analysis

Samples of the NANBH glycoprotein (4.2 $\mu$g) were hydrolyzed at 100° C. for 20 h with 500 $\mu$l $H_2O$ containing 20 $\mu$l 4N methanesulfonic acid and 10 mg Dowex 40×8 (200–400 mesh, H+ form). The hydrolysate was filtered through a millipore filter (0.45 $\mu$m) and 4.5 ml absolute ethanol was added. Neutral sugars were analyzed by post-column derivatization with Tetrazolium Blue and the derivatives were separated on a W3P cation exchange column in Waters chromatographic system as described by Boykins, R. A. et al (1980) J. Biochem. Biophys. Methods 2: 71–78. The glycoprotein contained about 2%±0.5 neutral sugars, predominantly mannose and about equal ratio of fucose and galactose.

Figure 1B:
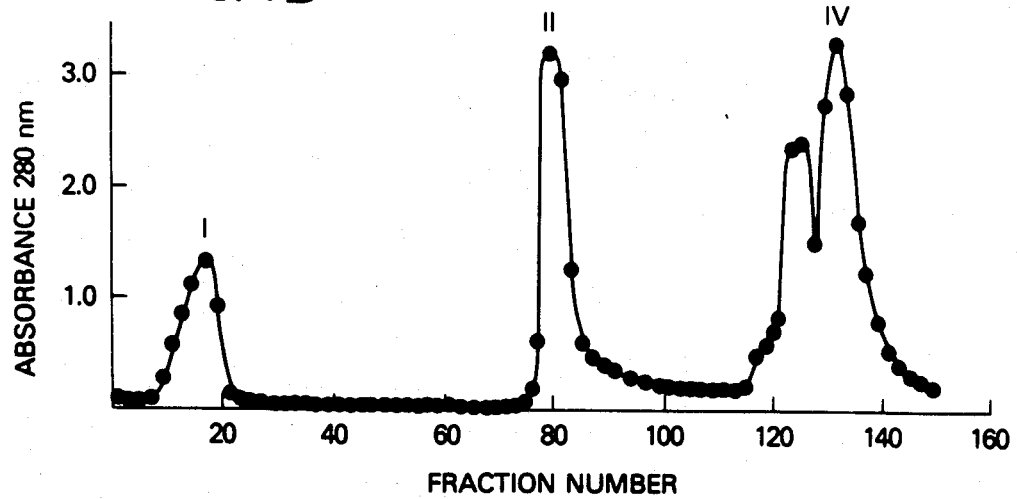

The characteristic elution profile for NANBH sera chromatographed on DEAE-cellulose appears in FIG. 1A, and that for sera from patients without NANBH or negative control individuals appears in FIG. 1B. Four major protein peaks were observed in inoculum I (FIG. 1A) and in three other sera from NANBH patients (Table I). Peak I contained the serum globulins as demonstrated by immunodiffusion against anti-human IgG. Peak II consistently appeared in all the sera chromatographed. Peak IV was shown by gel electrophoresis to contain albumin. Peak III was unique to sera from NANBH patients. This peak was found in all four sera shown to transmit NANBH to humans and/or to chimpanzees. It was not found, however, in the serum from one additional patient diagnosed NANBH but whose serum was not documented to transmit the disease (Table I).

Throughout the chromatographic procedures, each protein fraction obtained was tested for the presence of a NANBH-associated antigen by counterelectrophoresis (CEP). Antigen reactivity was found in protein peaks I, III, and IV of all four sera known to transmit NANBH (Table I). When protein peak III from inoculum I was further purified by Con A-Sepharose chromatography, two major protein peaks were resolved. The first peak was eluted without adsorption to the column matrix. Moreover, it did not show immunoprecipitin lines using the CEP assay. The second peak, which was positive in the CEP assay, was eluted with buffer containing 20 mM α-methyl mannoside. This indicated that the NANBH-associated soluble antigen is a glycoprotein. Neutral sugar analyses showed that 2%±0.5 of the glycoprotein is composed of mannose, galactose and fucose. The second peak from the Con A-Sepharose column was subsequently absorbed onto DEAE-cellulose. A single symmetrical protein peak was eluted with a linear gradient of 20 mM to 50 mM potassium phosphate buffers. The overall recovery of the purified antigen is approximately 720 μg from 10 ml of serum or 0.2% of the total serum protein.

Figure 2:
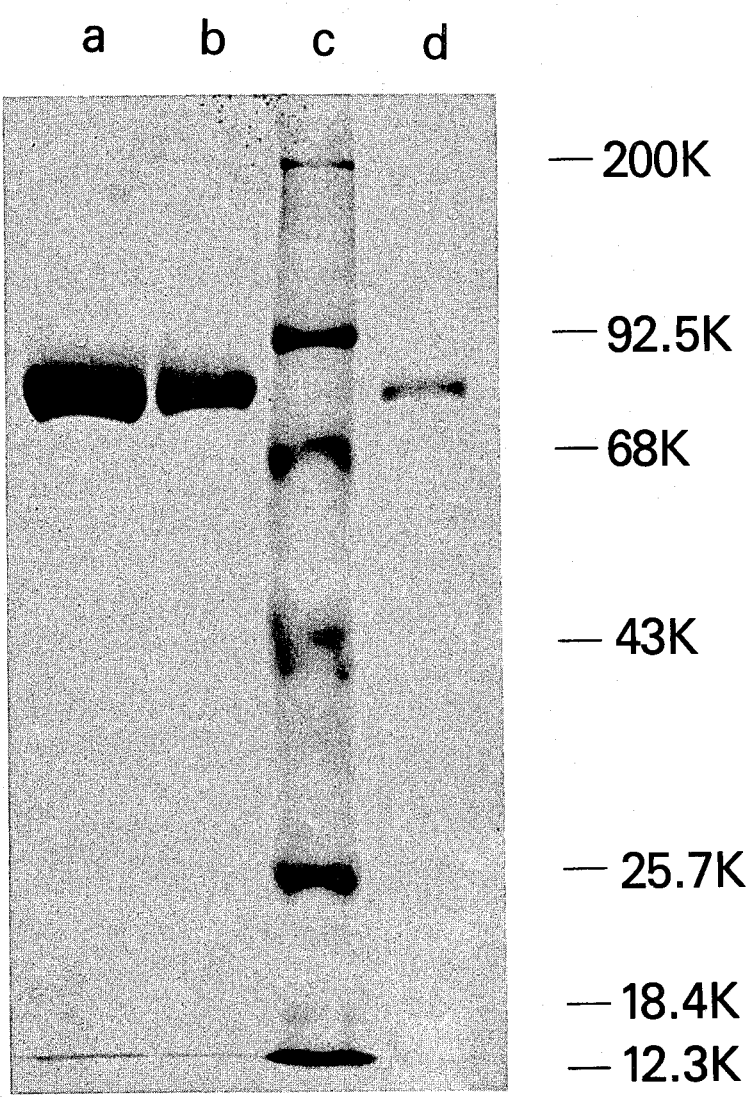
FIG. 2 shows sodium dodecyl sulfate-polyacrylamide gel electrophoresis of the NANBH-associated antigen from human serum (inoculum I). The position of marker proteins of known molecular weights are shown on the right. Lanes a, b and d show the position of the antigen subunit (monomer) at the following sample concentrations (a) 19.2 $\mu$g (b) 9.6 ug and (d) 2.4 $\mu$g.
Figure 3:
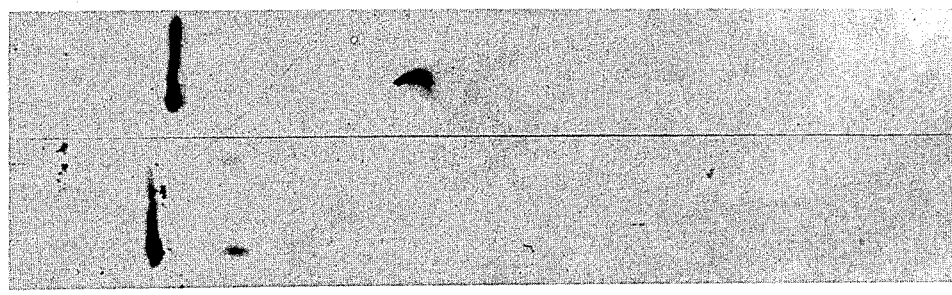
FIG. 3 shows the monomer of the glycoprotein being reactive with the rhesus monkey immune system by Western Blot.
Figure 3:
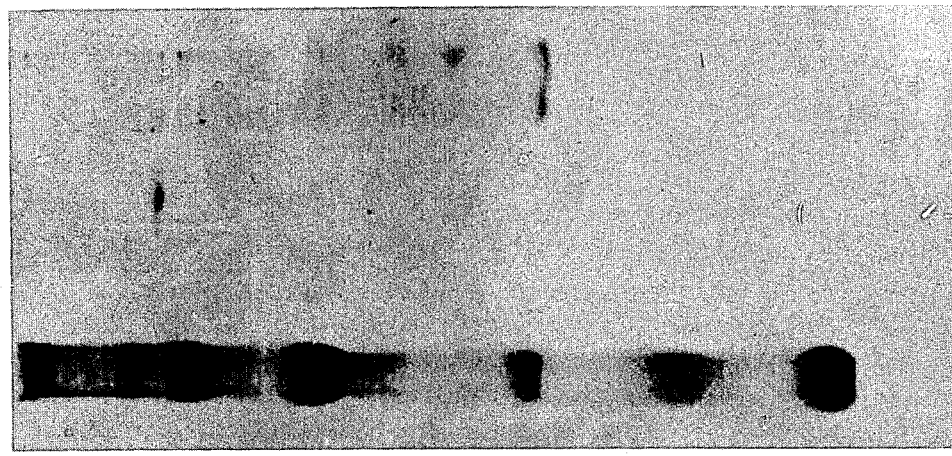

The migration of the purified glycoprotein (NANBH-associated antigen) on SDS-PAGE is shown in FIG. 2 compared with the migration of molecular weight of certain marker proteins. Based upon the mobilities of the marker proteins, linearly related to the logarithms of their respective molecular weights, the molecular weight of the glycoprotein monomer was calculated to be 77,000.

Figure 4:
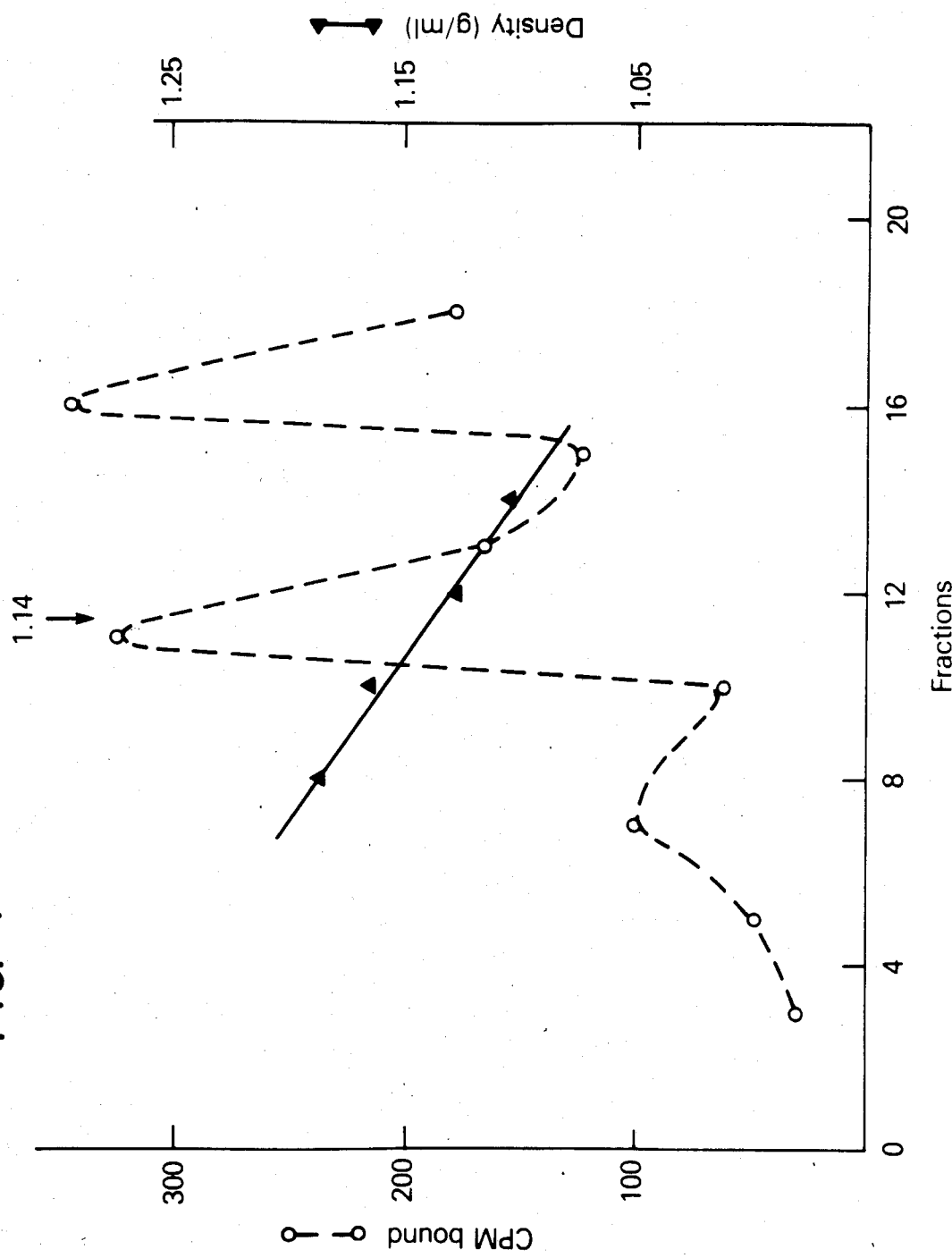
FIG. 4 shows sucrose density gradient banding of a documented infectious NANBH inoculum showing binding of radiolabelled rhesus monkey 877 immune serum to the NANBH-associated antigen both free in serum in a soluble form and on a particle at a density of 1.14 g/ml. Serum (300 $\mu$l) was layered on a 10 to 60 percent (by weight) sucrose gradient in 100 mM Tris-HCl, pH 7.4 containing 100 mM NaCl and 1 mM EDTA and centrifuged for 19 hours at 30,000 rpm in a SW 41 Ti rotor. Each fraction, following dialysis to remove sucrose, was reacted with the radiolabelled antibody to the NANBH-associated antigen.

Using the solid-phase RIA assay, radiolabelled 7S IgG from rhesus monkey 877 reacted only with sera from NANBH patients, and only with Peak III and not with peaks I, II or IV following DEAE chromatography. In addition the radiolabelled 7S IgG reacted with sucrose gradient fractions of inoculum I known to contain the infective agent of NANBH (FIG. 4). Antibody was bound to sucrose gradient fractions of density 1.14 g/ml, a density shown to be characteristic of the NANBH agent in these sera as described by Seto, et al (Lancet 2, 941–943 1984). In addition, binding was observed in the fractions on the top of the sucrose gradient consistent with the glycoprotein also existing as a soluble protein in addition to being present on the surface of virus particles at a density of 1.14 g/ml.

The following examples illustrate certain utilities of the present invention.

EXAMPLE 1

Using a solid-phase radioimmunoassay employing rhesus monkey antibody to the NANBH associated antigen, sera obtained at diagnosis from patients with viral hepatitis in Baltimore, Md. were tested for the presence of the NANBH-associated glycoprotein. The results appear in Table II. The glycoprotein antigen was not detected in the sera of any of 15 patients with either hepatitis A or hepatitis B. The antigen was detected in 2 of 86 control sera, in 15 of 15 sera from patients with chronic NANBH and in 3 of 28 sera from patients with NANBH who did not progress to chronicity. Possible explanations for the absence of the antigen in the sera of most patients with acute NANBH include:

(1) Incorrect diagnosis since the diagnoses were made by exclusion which results in lumping NANBH cases with other toxic liver diseases;

(2) A second agent responsible for antigen negative cases;

(3) Clearance of the antigen from the serum early in cases which do not progress to chronicity; or (4) Lack of sensitivity of the antigen test. However, the presence of the antigen in all 15 cases of chronic NANBH shows the specificity of the antigen for this disease and also the utility of serologic screening for this antigen to detect chronic carriers of NANBH or blood or plasma-derived products contaminated with the NANBH virus.

It may be noted that all patients positive for the antigen at diagnosis continued to have detectable antigen in their sera after the acute disease (follow-up proceeded for 6 months).

EXAMPLE II

To test the utility of the glycoprotein antigen as a vaccine, rhesus monkeys were immunized with the antigen and their serum used to protect chimpanzees against NANBH infection by "passive-immunization" described below. (This technique was necessitated since the rhesus monkeys themselves were not susceptible to infection by NANBH). For this study, a chimpanzee (No. 1292) was inoculated intravenously with a mixture of 1 ml ($10^2$ chimpanzee infectious doses) of a documented infectious NANBH inoculum (inoculum I) plus 1 ml of rhesus monkey "immune serum". This champanzee did not show any sign of infection, whereas a control chimpanzee (No. 1290) inoculated with a mixture of the identical inoculum (inoculum I) plus 1 ml of rhesus monkey "pre-immune" serum, developed hepatitis as indicated by elevated serum aminotransferase (liver enzyme) beginning at week 12 after inoculation. The mixtures in both cases were prepared and incubated at 37° C. for 1 hour followed by 18 hours at 4° C. prior to inoculation intravenously into the respective chimpanzees. "Immune serum" contained antibodies to the NANBH-associated glycoprotein, whereas "pre-immune" serum was obtained from the same rhesus monkey as the immune serum but prior to immunization with the NANBH-associated glycoprotein. Therefore, it contained all serum components but no specific antibodies to the glycoprotein.

Among various advantages of the present invention is included a highly specific kit for detecting the presence of or identifying the carrier of source of NANBH or infective factor thereof. The kit, inter alia, comprises container(s) containing the isolated, purified glycoprotein as described herein and/or antibodies prepared by using said glycoprotein as an immunogen. The kit, of course, may also include such other accessories as are routine and common in such kits, e.g., reagents and buffers, microtiter plates, plate reader, micropipettes, fluorescent or radioactive markers and the like.

A pharmaceutical preparation, e.g., a vaccine for preventing or controlling NANBH comprising the isolated, purified antigen of the present invention in a pharmaceutically acceptable carrier, e.g., physiological saline and the like, for administration to a subject in an amount suitable to induce protective antibodies in said subject can also be prepared in accordance with the teachings of the present invention.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated, purified non-A, non-B hepatitis (NANBH) associated antigen having the following properties:
    (a) molecular weight of the monomer on sodium dodecyl sulphate polyacrylamide gel being about 77,000;
    (b) the monomer being reactive with rhesus monkey immune serum;
    (c) being a glycoprotein containing about 2% carbohydrate comprising substantially mannose and about equal ratio of fucose and galactose;

(d) having an aromatic amino acid composition comprising molecular ratios of phenylalanine, tyrosine and tryptophan of about 3:3:1 respectively; and (e) being an immunogen.

2. Antibodies specifically reactive to antigen of claim 1.

3. A pharmaceutical composition comprising immunogenic amount of isolated, purified antigen of claim 1 and a pharmaceutically acceptable carrier.

4. A kit for screening or detecting a carrier, source or causative factor of non-A, non-B hepatitis comprising a container containing an isolated, purified antigen of claim 1.

5. The kit of claim 4 further comprising a container containing antibodies specifically reactive to said antigen.

* * * * *